(12) United States Patent
Gao et al.

(10) Patent No.: US 8,748,666 B2
(45) Date of Patent: Jun. 10, 2014

(54) PREPARATION METHODS OF METHYL-D3-AMINE AND SALTS THEREOF

(75) Inventors: Xiaoyong Gao, Kunshan (CN); Weidong Feng, Kunshan (CN); Xiaojun Dai, Kunshan (CN)

(73) Assignee: Suzhou Zelgen Biopharmaceutical Co., Ltd., Kunshan (CN)

( * ) Notice: Subject to any disclaimer, the term of this patent is extended or adjusted under 35 U.S.C. 154(b) by 0 days.

(21) Appl. No.: 13/635,880

(22) PCT Filed: Mar. 17, 2011

(86) PCT No.: PCT/CN2011/071928
§ 371 (c)(1),
(2), (4) Date: Sep. 18, 2012

(87) PCT Pub. No.: WO2011/113369
PCT Pub. Date: Sep. 22, 2011

(65) Prior Publication Data
US 2013/0018209 A1    Jan. 17, 2013

(30) Foreign Application Priority Data
Mar. 18, 2010 (CN) .......................... 2010 1 0127698

(51) Int. Cl.
C07C 209/64    (2006.01)
C07B 59/00    (2006.01)

(52) U.S. Cl.
USPC ........................................................ 564/487

(58) Field of Classification Search
None
See application file for complete search history.

(56) References Cited

FOREIGN PATENT DOCUMENTS

WO    WO 03/016246 A1    2/2003

OTHER PUBLICATIONS

Perrin et al., Journal of the American Chemical Society (2005), 127(26), p. 9641-9647.*
International Search Report for PCT/CN2011/071928 issued Jun. 23, 2011.
J.A. Elvidge et al., Isotopes: Essential Chemistry and Applications, Beijing: Atomic Energy Publishing House, 1987, 2nd edition, p. 295, table 4 and p. 296.
Isotope Chemistry, Beijing: Science Publishing House, Mar. 1956, 1st edition, pp. 255-256.
Leonard C. Leitch et al., Contribution to the Synthesis of Organic Deuterium Compounds, I. Deuteropolymethylene, Canadian Journal of Research, Section B: Chemical Sciences, 1950, vol. 28B, pp. 256-263.
Guangzhou Ge, The Application of Nitromethane in Organic Synthesis, Chemical Industry Times, 1992, No. 6, pp. 11-16.
Jeffrey C. Pelletier et al., Mitsunobu Reaction Modifications Allowing Product Isolation Without Chromatography: Application to a Small Parallel Library, Chemical Sciences Division, Wyeth-Ayerst Research, Tetrahedron Letters, 2000, vol. 41, No. 6, pp. 797-800, Table 1.
Masaki Kuwabara et al., Synthesis of Polyfluoroalkylamines by the Gabriel Method, The Chemical Society of Japan, Nippon Kagaku Kaishi, 1985, No. 4, pp. 796-798.
Rivara Mirko et al., A Short and Efficient Synthesis of the Selective $H_4$ Receptor Agonist 4-Methylhistamine, Letters in Organic Chemistry, 2009, No. 6, pp. 88-89.
Chinese Office Action Dated Feb. 18, 2014 in Chinese Application No. 201110302329.X, dated Feb. 18, 2014 (3 pages) (in English).
EPO Communication Dated Mar. 5, 2014 in European Application No. 11755686.0-1451 forwarding European Search Report Dated Feb. 13, 2014 (3 pages)(in English).
J. Saavedra, "Lithiation of α-Nitrosaminoalkyl Ethers. Synthetic Equivalents of α-Primary Amino Carbanions," J. Org. Chem., 48, pp. 2388-2392 (1983).
A. Martin et al., "Stereoselective Synthesis of L-[$1-^{13}C$], L-[$2-^{13}C$] and L-[$^{15}N$] Amino Acids," Isotopes Environ. Health Stud., vol. 32, pp. 15-19 (1996).
F. J. Marshal et al., "Ethyl Chlorocarbonate-$^{14}C$ and its Application to the Synthesis of N-Methyl-$^{14}C$-Amines," Journal of Labelled Compounds, vol. VI, No. 3, (Jul.-Sep. 1970).
S. W. Rhee et al., Synthesis of [$^{14}C$] Anthracycline Anticancer Agent 14-O-(β-Alanyl-N-HCl)-7-O-(2',6'-Dideoxy-2'-Fluoro-α-L-Talopyranosyl) Adriamycinone-14-$^{14}C$(DA-125-$^{14}C$), Journal of Labelled Compounds and Radiopharmaceuticals, vo. XXXIX, No. 9 pp. 773-785 (1997).
S. Niwayama, Synthesis of d-Labeled N-Alylmaleimides and Application to Quantitative Peptide Analysis by Isotope Differential Mass Spectrometry, Biooranic & Medicinal Chemistry Letters, vol. 11, pp. 2257-2261 (2001).

* cited by examiner

Primary Examiner — Brian J Davis
(74) Attorney, Agent, or Firm — Flaster/Greenberg, P.C.

(57) ABSTRACT

Preparation methods of methyl-$d_3$-amine and salts thereof are provided, which contain the following steps: (i) nitromethane is subjected to react with deuterium oxide in the present of bases and phase-transfer catalysts to form nitromethane-$d_3$, which is subsequently subjected to reduction in an inert solvent to form methyl-$d_3$-amine, and optionally, methyl-$d_3$-amine reacts subsequently with acids to form salts of methyl-$d_3$-amine; or (ii) N-(1,1,1-trideuteriomethyl)phthalimide is subjected to react with acids to form salts of methyl-$d_3$-amine. The present methods are easy, high efficient, and low cost.

7 Claims, No Drawings

PREPARATION METHODS OF METHYL-D3-AMINE AND SALTS THEREOF

BACKGROUND OF THE INVENTION

1. Field of the Invention

The invention relates to the synthetic methods and manufacture procedures for (methyl-$d_3$)amine and salts thereof.

2. Description of Related Art (Methyl-$d_3$)amine and the hydrochloride thereof, the important intermediates for chemical synthesis, can be used to make medicinal compounds.

For example, the ω-diphenylurea derivatives are known as the compounds with c-RAF kinase inhibition activity. Initially, ω-diphenylurea compounds, such as Sorafenib, were firstly found as the inhibitors of c-RAF kinase. The other studies had shown that they could also inhibit the MEK and ERK signal transduction pathways and activities of tyrosine kinases including vascular endothelial growth factor receptor-2 (VEGFR-2), vascular endothelial growth factor receptor-3 (VEGFR-3), and platelet-derived growth factor receptor-β (PDGFR-β) (Curr Pharm Des 2002, 8, 2255-2257). Therefore, it is called multi-kinase inhibitor which possesses dual anti-tumor effects.

Sorafenib (trade name Nexavar), a novel oral multi-kinase inhibitor, was developed by Bayer and Onyx. In December 2005, based on its outstanding performance in phase III clinical trials for treating advanced renal cell carcinoma, Sorafenib was approved by FDA for treating advanced renal cell carcinoma. It was marketed in China in November 2006. However, Sorafenib has various side-effects, such as hypertension, weight loss, rash and so on.

(Methyl-d3)amine is used during the preparation of sorafenib derivatives. However, the synthetic steps or the current preparation processes are relatively complex, or the cost is high. Therefore, development of some simple, highly efficient, and/or low cost methods for preparing (methyl-d3)amine and salts thereof is needed.

BRIEF SUMMARY OF THE INVENTION

The subject of the invention is to provide a simple, highly efficient and/or low cost method for preparing (methyl-$d_3$)amine and salts thereof.

In the first aspect, the invention provides a method for preparing (methyl-$d_3$)amine or salts thereof, comprising:

(i) in the presence of a base and a phase transfer catalyst, reacting nitromethane with deuterated water to form deuterated nitromethane;

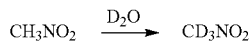

(ii-a) in an inert solvent, reducing deuterated nitromethane to form (methyl-$d_3$)amine; then optionally reacting (methyl-$d_3$)amine with an acid to form the salt of (methyl-$d_3$)amine; or (ii-b) in an inert solvent and in the presence of an acid, reducing deuterated nitromethane to form the salt of (methyl-$d_3$)amine directly.

In one embodiment, said base is selected from sodium hydride, potassium hydride, deuterated sodium hydroxide, deuterated potassium hydroxide, potassium carbonate or the combination thereof.

In one embodiment, in step (ii-a) or (ii-b), zinc powder, magnesium powder, iron, or nickel is used as a catalyst.

In one embodiment, said acid is selected from hydrochloric acid, sulfuric acid, formic acid, acetic acid, or the combination thereof.

In one embodiment, in step (ii-a) or (ii-b), said inert solvent is selected from methanol, ethanol, water, tetrahydrofuran, isopropanol, or the combination thereof.

In the second aspect, the invention provides a method for preparing (methyl-$d_3$)amine or salts thereof, comprising:

(a1) in an inert solvent and in the presence of a catalyst, reacting phthalimide with deuterated methanol to form N-(methyl-$d_3$)phthalimide;

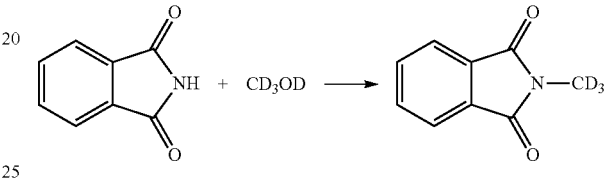

or (a2) in an inert solvent, reacting an alkali metal salt of phthalimide with compound A,

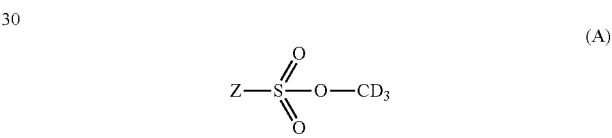

wherein, Z is $CH_3$, $O-CD_3$ or

wherein R is methyl, nitro or halogen (F, Cl or Br), to form N-(methyl-$d_3$)phthalimide;

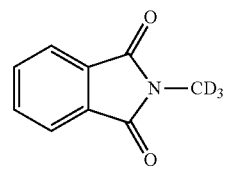 [SMILES: [2H]C([2H])([2H])N1C(=O)c2ccccc2C1=O]

(b) reacting N-(methyl-$d_3$)phthalimide with an acid to form the salt of (methyl-$d_3$)amine; and optional (c): reacting the salt of (methyl-$d_3$)amine with a base to form (methyl-$d_3$)amine.

In one embodiment, in step (a1), said inert solvent is tetrahydrofuran.

In one embodiment, said acid is selected from hydrochloric acid, sulfuric acid, formic acid, acetic acid, or combination thereof.

In one embodiment, in step (a1), said catalyst is selected from diethyl azodicarboxylate (DEAD), diisopropyl azodicarboxylate (DIAD), triphenylphosphine, tributylphosphine, or the combination thereof.

In one embodiment, in step (a2), said inert solvent is selected from N,N-dimethylformamide (DMF), N,N-dimethylacetamide (DMA), dimethylsulfoxide (DMSO), N-methylpyrrolidone (NMP), or the combination thereof.

In one embodiment, in step (a2), the reaction temperature is −10° C. to reflux temperature, preferably, −4° C. to 100° C., and more preferably, 20~80° C.

In one embodiment, the reaction time is 0.1-24 hours, preferably, 0.3~5 hours, and more preferably, 0.5~2 hours.

In one embodiment, in step (a2), said alkali metal salt of phthalimide includes potassium phthalimide, sodium phthalimide, lithium phthalimide, or the combination thereof.

In one embodiment, in step (a2), said compound A includes (methyl-$d_3$) 4-methylbenzenesulfonate, (methyl-$d_3$) 3-nitrobenzenesulfonate, or (methyl-$d_3$) 4-nitrobenzenesulfonate.

In one embodiment, there is another step prior to step (a2) of the said method: under a basic condition and in an inert solvent, reacting deuterated methanol with tosyl chloride to form (methyl-$d_3$) 4-methylbenzenesulfonate. Preferably, said inert solvents in such step include water, tetrahydrofuran, or the combination thereof.

In the third aspect, the invention provides a method for preparing a salt of (methyl-$d_3$)amine, comprising:

In an aqueous solvent, reacting N-(methyl-$d_3$)phthalimide with an acid to form a salt of (methyl-$d_3$)amine, wherein said acid includes hydrochloric acid, sulfuric acid, hydrobromic acid, trifluoroacetic acid, or the combination thereof.

In one embodiment, the reaction temperature is 30° C. to reflux temperature (such as 120° C.), and preferably, 40~110° C.

In one embodiment, the reaction time is 0.5~48 hours, preferably, 1~36 hours, and more preferably, 2~24 hours.

In one embodiment, said method includes:

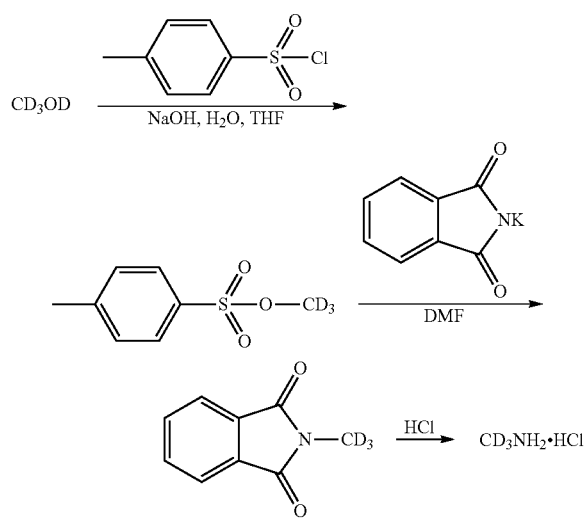

In the fourth aspect, the invention provides a method for preparing N-(4-chloro-3-(trifluoromethyl)phenyl)-N-(4-(2-(N-(methyl-$d_3$)aminoformyl)-4-pyridyloxy)phenyl)urea using (methyl-$d_3$)amine or salts thereof prepared according to the invention:

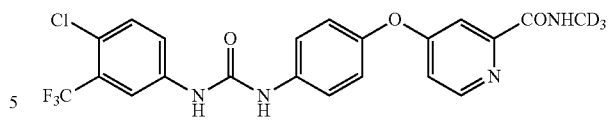

It should be understood that in the present invention, any of the technical features specifically described above and below (such as in the Examples) can be combined with each other, thereby constituting new or preferred technical solutions that are not described one by one in the specification.

DETAILED DESCRIPTION OF THE INVENTION

The inventors developed a simple, highly efficient and low cost method and procedure for producing (methyl-$d_3$)amine and salts thereof. Based on this discovery, the inventors completed the present invention.

Furthermore, the inventors synthesized deuterated ω-diphenylurea compounds which could be used as the efficient kinase inhibitors. Taking the most preferred deuterated ω-diphenylurea compound N-(4-chloro-3-(trifluoromethyl)phenyl)-N'-(4-(2-(N-(methyl-$d_3$)aminoformyl)-4-pyridyloxy)phenyl)urea (CM4307) and un-deuterated compound N-(4-chloro-3-(trifluoromethyl)phenyl)-N'-(4-(2-(N-methyl aminoformyl)-4-pyridyloxy)phenyl)urea (CM4306) as an example, Compound CM4307

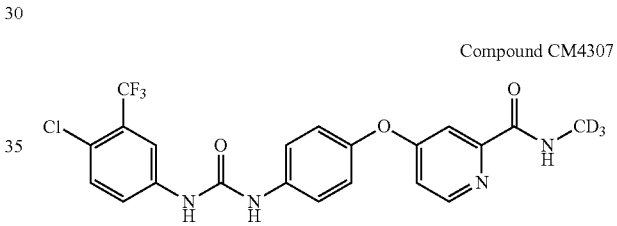

the results of pharmacokinetic test showed that the half life ($T_{1/2}$) of CM4307 was longer, the $AUC_{0-\infty}$ of CM4307 increased significantly and the apparent clearance of CM4307 decreased compared to CM4306.

The results of pharmacodynamic test performed in the nude mouse model inoculated with human liver cancer cell SMMC-7721 showed that, after intragastric administration at 100 mg/kg per day for two weeks, the relative tumor increment rate T/C (%) as an evaluation index of CM4306 anti-tumor activity was 32.2%, while that of CM4307 was 19.6%. Therefore, the absolute value of anti-tumor activity increased over 10%, the relative value increased about 60% (32.2%/19.6%−1=64%), and CM4307 showed more significant tumor inhibition effect.

DEFINITIONS

As used herein, the team "halogen" refers to F, Cl, Br and I. Preferably, halogen is selected from F, Cl, and Br.

As used herein, the term "alkyl" refers to straight-chain or branched chain alkyl.

Preferable alkyl is C1-C4 alkyl, such as methyl, ethyl, propyl, iso-propyl, butyl, iso-butyl, tert-butyl, etc.

As used herein, the term "deuterated" means that one or more hydrogens of compounds or groups are substituted by deuterium or deuteriums. "Deuterated" can be mono-substituted, hi-substituted, multi-substituted or total-substituted.

The terms "one or more deuterium-substituted" and "substituted by deuterium once or more times" can be used interchangeably.

In one embodiment, the deuterium content in a deuterium-substituted position is at least greater than the natural abundance of deuterium (0.015%), preferably >50%, more preferably >75%, more preferably >95%, more preferably >97%, more preferably >99%, more preferably >99.5%.

As used herein, the term "compound CM4306" is 4-(4-(3-(4-chloro-3-(trifluoromethyl)phenyl)ureido)-phenoxy)-2-(N-methyl)picolinamide.

As used herein, the term "compound CM4307" is 4-(4-(3-(4-chloro-3-(trifluoromethyl)phenyl)ureido)-phenoxy)-N-(methyl-d$_3$)picolinamide.

As used herein, the term "TsOH" represents p-toluenesulfonic acid. Therefore, CM4307.TsOH represents the p-toluenesulfonate of CM4307. CM4309.TsOH represents the p-toluenesulfonate of CM4309.

A key intermediate of the invention is N-(methyl-d$_3$)phthalimide;

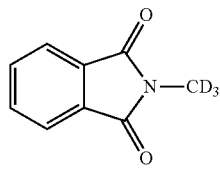 [SMILES: [2H]C([2H])([2H])N1C(=O)c2ccccc2C1=O]

This intermediate can be called "deuterated methyl phthalimide". Except for H, all or almost all (>99 wt %) of the elements (such as N, C, O, etc.) in the above compounds are naturally existed elements with highest abundance, such as $^{14}$N, $^{12}$C and $^{16}$O.

Preparation

The preparation methods for the compound of the invention are described in detail as below. However, these specific methods are not provided for the limitation of the invention. The compounds of the invention can be readily prepared by optionally combining any of the various methods described in the specification or with various methods known in the art, and such combination can easily be carried out by the skilled in the art.

In general, during the preparation, each reaction is conducted in an inert solvent, at a temperature between room temperature to reflux temperature (such as 0~80° C. preferably 0~50° C.). Generally, the reaction time is 0.1~60 hours, preferably, 0.5~48 hours.

Taking CM4307 as an example, an optimized preparation route is shown as follows:

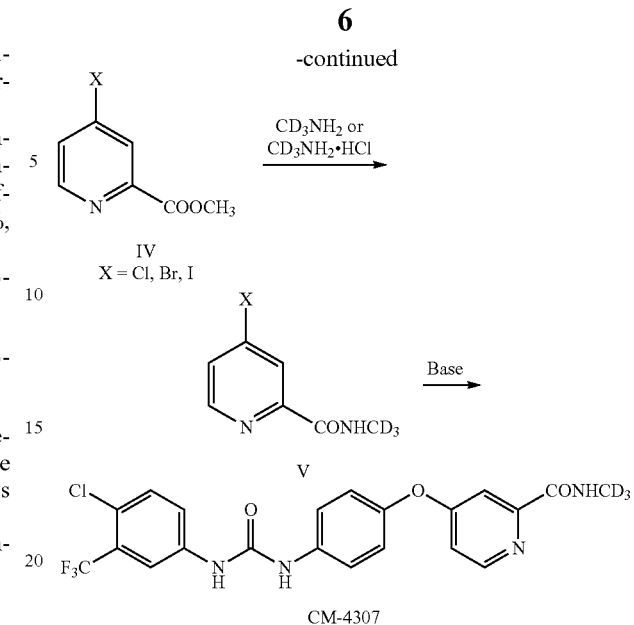

As shown in Scheme 1, in the presence of N,N'-carbonyldiimidazole, phosgene or triphosgene, 4-aminophenol (Compound I) reacts with 3-trifluoromethyl-4-chloro-aniline (Compound II) to give 1-(4-chloro-3-(trifluoromethyl)phenyl)-3-(4-hydroxyphenyl)urea (Compound III). 2-(N-(methyl-d$_3$))carbamoyl pyridine (Compound V) is obtained by reacting methyl picolinate (Compound IV) with (methyl-d$_3$) amine or (methyl-d$_3$)amine hydrochloride directly or in the presence of the base such as sodium carbonate, potassium carbonate, sodium hydroxide, triethylamine, pyridine and the like. In the presence of base (such as potassium tert-butoxide, sodium hydride, potassium hydride, potassium carbonate, cesium carbonate, potassium phosphate, potassium hydroxide, sodium hydroxide) and an optional catalyst (such as cuprous iodide and proline, or cuprous iodide and picolinic acid), Compound III reacts with Compound V to form compound CM-4307. The above reactions are conducted in an inert solvent, such as dichloromethane, dichloroethane, acetonitrile, n-hexane, toluene, tetrahydrofuran, N,N-dimethylformamide, dimethyl sulfoxide and so on, and at a temperature of 0-200° C.

Another particularly preferred process for preparing CM4307 is shown as below:

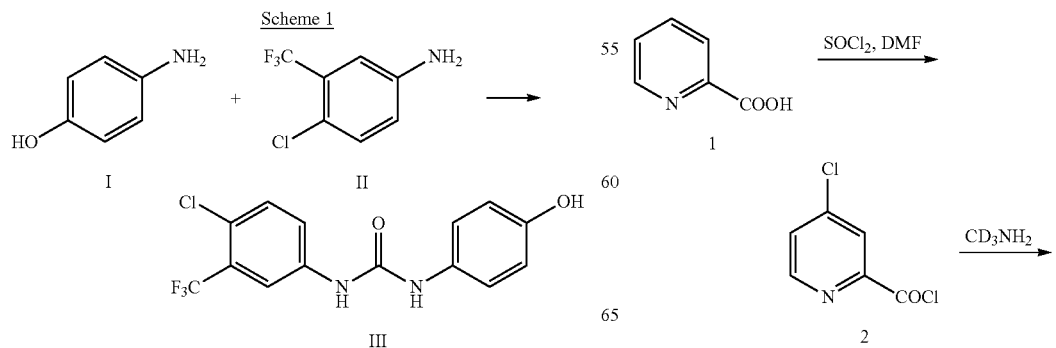

-continued

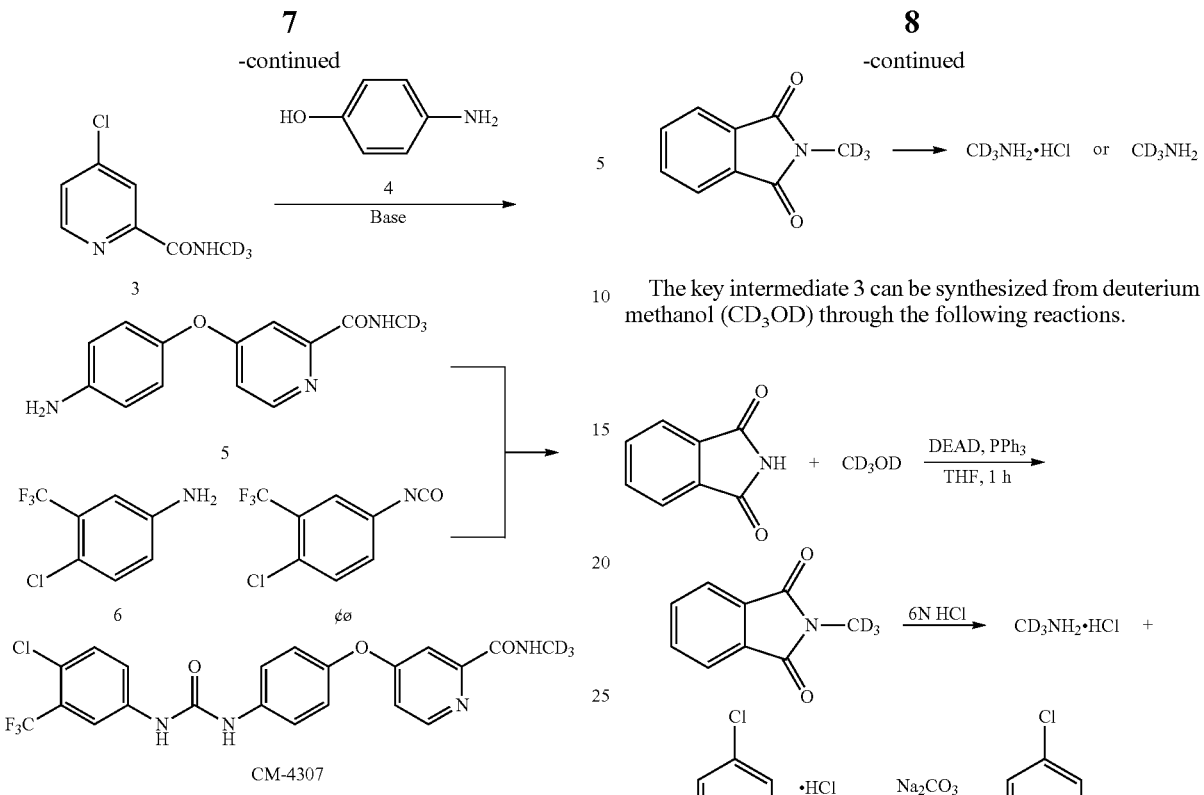

wherein, the deuterium can be introduced by using deuterated methylamine. Deuterated methylamine can be prepared using a method known in the art as below, for example, hydrogenation of deuterated nitromethane shown as follows:

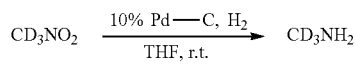

wherein r.t. means room temperature.

Alternatively, deuterated methylamine or the hydrochloride thereof can be prepared through the following reactions. Deuterated nitromethane is obtained by reacting nitromethane with deuterium water in the presence of base (such as sodium hydride, potassium hydride, deuterated sodium hydroxide, deuterated potassium hydroxide, potassium carbonate and the like) or phase-transfer catalyst. The above experiment can be repeated if necessary, to produce deuterated nitromethane in high purity. Deuterated nitromethane is reduced in the presence of zinc powder, magnesium powder, iron, or nickel and the like to form deuterated methylamine or the hydrochloride thereof.

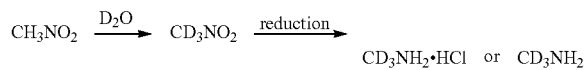

Furthermore, deuterated methylamine or the hydrochloride thereof can be obtained through the following reactions.

The key intermediate 3 can be synthesized from deuterium methanol ($CD_3OD$) through the following reactions.

The detailed preparation procedure is described in Example 1.

The main advantages of the method for preparing (methyl-$d_3$)amine or salts thereof of the invention include:

(1) The method is simple, highly efficient and low cost.
(2) The purity of the product is high.
(3) The method can be used in various applications.

The present invention will be further illustrated below with references to the specific examples. It should be understood that these examples are only to illustrate the invention but not to limit the scope of the invention. The experimental methods with no specific conditions described in the following examples are generally performed under the conventional conditions, or according to the manufacture's instructions. Unless indicated otherwise, parts and percentage are calculated by weight.

Example 1

Preparation of N-(4-chloro-3-(trifluoromethyl)phenyl)-N'-(4-(2-(N-(methyl-$d_3$)aminoformyl)-4-pyridyloxy)phenyl)urea (Compound CM4307)

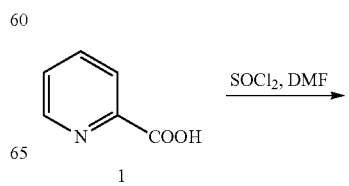

-continued

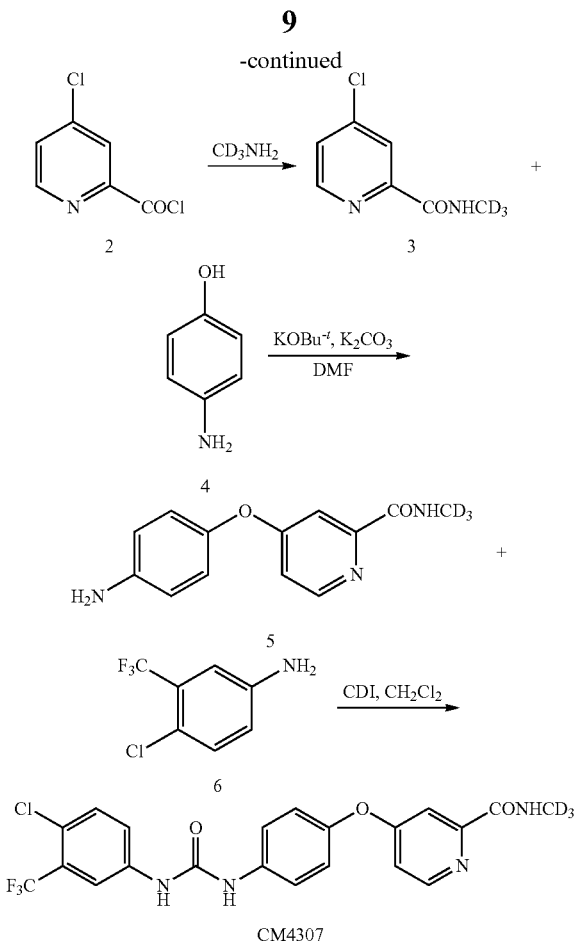

1. Preparation of 4-chloropyridine-2-(N-(methyl-d₃))carboxamide (3)

To a 250 mL single-neck round-bottom flask equipped with waste gas treatment equipments, thionyl chloride (60 MO was added. Anhydrous DMF (2 mL) was dropwise added slowly while keeping the temperature at 40-50° C. After addition, the mixture was stirred for 10 min, and then nicotinic acid (20 g, 162.6 mmol) was added in portions in 20 min. The color of the solution gradually changed from green into light purple. The reaction mixture was heated to 72° C., and refluxed for 16 hours with agitation. A great amount of solid precipitated. The mixture was cooled to room temperature, diluted with toluene (100 mL) and concentrated to almost dry. The residue was diluted with toluene again and concentrated to dry. The residue was filtered and washed with toluene to give 4-chloro-pyridine-2-carbonyl chloride as a light yellow solid. The solid was slowly added into a saturated solution of (methyl-d₃)amine in tetrahydrofuran in an ice-bath. The mixture was kept below 5° C. and stirred for 5 hours. Then, the mixture was concentrated and ethyl acetate was added to give a white solid precipitate. The mixture was filtered, and the filtrate was washed with saturated brine, dried over sodium sulfate and concentrated to give 4-chloropyridine-2-(N-(methyl-d₃))carboxamide (3) (20.68 g, 73% yield) as a light yellow solid.

$^1$H NMR (CDCl₃, 300 MHz): 8.37 (d, 1H), 8.13 (s, 1H), 7.96 (br, 1H), 7.37 (d, 1H).

2. Preparation of 4-(4-aminophenoxy)-2-pyridine-(N-(methyl-d₃))carboxamide (5)

To dry DMF (100 mL), 4-aminophenol (9.54 g, 0.087 mol) and potassium tert-butoxide (10.3 g, 0.092 mol) was added in turn. The color of the solution turned into deep brown. After stirring at room temperature for 2 hours, to the reaction mixture was added 4-chloro-(N-methyl-d₃)pyridine-2-carboxamide (3) (13.68 g, 0.079 mol) and anhydrous potassium carbonate (6.5 g, 0.0467 mol), then warmed up to 80° C. and stirred overnight. TLC detection showed the reaction was complete. The reaction mixture was cooled to room temperature, and poured into a mixed solution of ethyl acetate (150 mL) and saturated brine (150 mL). The mixture was stirred and then stood for separation. The aqueous phase was extracted with ethyl acetate (3×100 mL). The extracted layers were combined, washed with saturated brine (3×100 mL) prior to drying over anhydrous sodium sulfate, and concentrated to afford 4-(4-aminophenoxy)-2-pyridine-(N-(methyl-d₃))carboxamide (18.00 g, 92% yield) as a light yellow solid.

$^1$H NMR (CDCl₃, 300 MHz): 8.32 (d, 1H), 7.99 (br, 1H), 7.66 (s, 1H), 6.91-6.85 (m, 3H), 6.69 (m, 2H), 3.70 (br, s, 2H).

3. Preparation of N-(4-chloro-3-(trifluoromethyl)phenyl)-N'-(4-(2-(N-(methyl-d₃)aminoformyl)-4-pyridyloxy)phenyl)urea (CM4307)

To methylene chloride (120 mL), 4-chloro-3-trifluoromethyl-phenylamine (15.39 g, 78.69 mmol) and N,N'-carbonyldiimidazole (13.55 g, 83.6 mmol) was added. After stirring at room temperature for 16 hours, a solution of 4-(4-aminophenoxy)-2-pyridine-(N-(methyl-d₃))-carboxamide (18 g, 73 mmol) in methylene chloride (180 mL) was slowly added dropwise. The mixture was stirred at room temperature for another 18 hours. TLC detection showed the reaction was complete. The mixture was concentrated to about 100 mL by removing methylene chloride through a rotary evaporator and stood for several hours at room temperature. A great amount of white solid precipitated. The solid was filtered and washed with abundant methylene chloride. The filtrate was concentrated by removing some solvent, and some solid precipitated again. Two parts of solid were combined and washed with abundant methylene chloride to afford N-(4-chloro-3-(trifluoromethyl)phenyl)-N'-(4-(2-(N-(methyl-d₃)aminoformyl)-4-pyridyloxy)phenyl)urea (CM4307, 20.04 g, 58% yield) as a white powder (pure product).

$^1$H NMR (CD₃OD, 300 MHz): 8.48 (d, 1H), 8.00 (d, 1H), 7.55 (m, 5H), 7.12 (d, 1H), 7.08 (s, 2H), ESI-HRMS m/z: $C_{21}H_{13}D_3ClF_3N_4O_3$, Calcd. 467.11. Found 490.07 (M+Na)⁺.

Furthermore, Compound CM4307 was dissolved in methylene chloride and reacted with benzoperoxoic acid to afford the oxidized derivative: 4-(4-(3-(4-chloro-3-(trifluoromethyl)phenyl)ureido)phenoxy)-2-(N-(methyl-d₃)aminoformyl)pyridine-1-oxide,

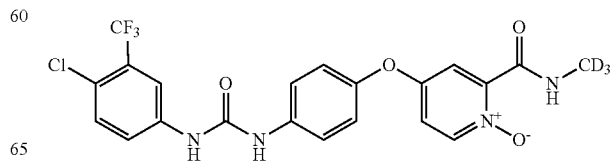

Example 2

Preparation of 4-chloropyridyl-(N-(methyl-d₃))-2-carboxamide (3)

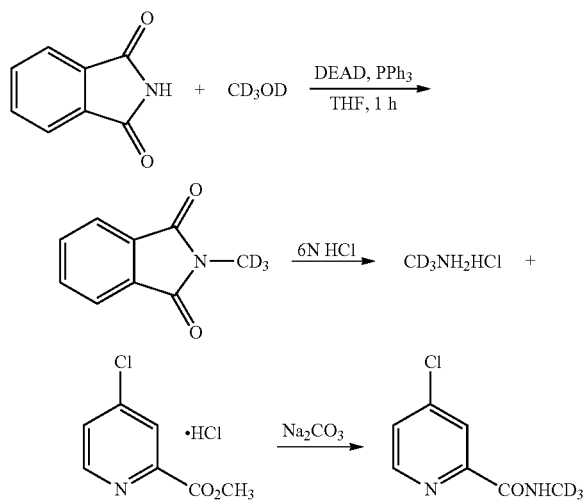

a) To a solution of phthalimide (14.7 g, 0.1 mol), deuterated methanol (3.78 g, 0.105 mol, 1.05 eq) and triphenylphosphine (28.8 g, 0.11 mol, 1.1 eq) in anhydrous tetrahydrofuran was dropwise added a solution of DEAD (1.1 eq) in tetrahydrofuran under ice-bath. After addition, the mixture was stirred for 1 hour at room temperature. The mixture was purified by chromatography column, or the solvent in the mixture was removed, and then to the residue was added an appropriate amount of DCM and cooled in the refrigerator to precipitate the solid. The mixture was filtered and the filtrate was concentrated by a rotary evaporator, and then the residue was purified by flash chromatography column to afford the pure product of 2-(N-(methyl-d₃))-isoindole-1,3-dione, (14.8 g, 90% yield).

b) 2-(N-(methyl-d₃))-isoindole-1,3-dione (12.5 g, 0.077 mol) was dissolved hydrochloric acid (6 N, 50 mL) and the mixture was refluxed for 24-30 hours in a sealed tube. The reaction mixture was cooled to room temperature and then cooled below 0° C. in the refrigerator to precipitate the solid. The solid was filtrated and washed with cold deionized water. The filtrate was collected and concentrated by rotary evaporator to remove water. The residue was dried to afford (methyl-d₃)amine hydrochloride salt. Anhydrous DCM (100 mL) was added in (methyl-d₃)amine hydrochloride salt and 4-chloro-pyridine-2-carboxylic acid methyl ester hydrochloride salt (6.52 g, 0.038 mol, 0.5 eq) and sodium carbonate (12.2 g, 0.12 mol, 1.5 eq) were added. The reaction flask was sealed and placed in the refrigerator for one day. After the reaction was complete by TLC detection, the reaction mixture was washed with water, dried, concentrated and purified by chromatography column to afford 4-chloro-pyridine-2-(N-(methyl-d₃))formamide (compound (3), 5.67 g, 86% yield). The structural feature was the same as Example 1.

Example 3

Preparation of (methyl-d₃)amine hydrochloride

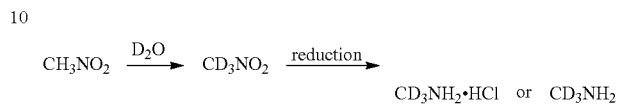

1. Nitromethane-d₃

Nitromethane (0.61 g, 10 mmol, 1.0 eq) was dissolved in heavy water (5.0 g, 250 mmol, 25.0 eq). After Nitrogen replacement was conducted for three times, the mixture was refluxed for 16 hours. The reaction mixture was cooled to room temperature, and extracted with anhydrous ethyl ether (20 mL×2). The organic phase was dried over anhydrous sodium sulfate and filtered. The solvent in the filtrate was removed under reduced pressure to afford the title compound (0.1 g) as a yellow liquid. The result of NMR indicated that partially-deuterated nitromethane and totally-deuterated nitromethane was obtained.

2. (Methyl-d₃)amine hydrochloride

Deuterated nitromethane (0.64 g, 10.0 mmol) was dissolved in methanol (25.0 mL). Pd/C (10%, 0.1 g) was added. $H_2$ replacement was conducted for three times through balloon. At the room temperature, the mixture was stirred for 16 hours. The mixture was acidified by dropping hydrochloric acid, and filtered. The solvent in the filtrate was removed under reduced pressure to afford the title compound (0.60 g) as a light yellow product. The result of NMR indicated that (methyl-d₃)amine hydrochloride was obtained.

$^1$H NMR (DMSO-d₆, 400 MHz): δ 8.05 (br, 2H)

Example 4

Preparation of (methyl-d₃)amine hydrochloride

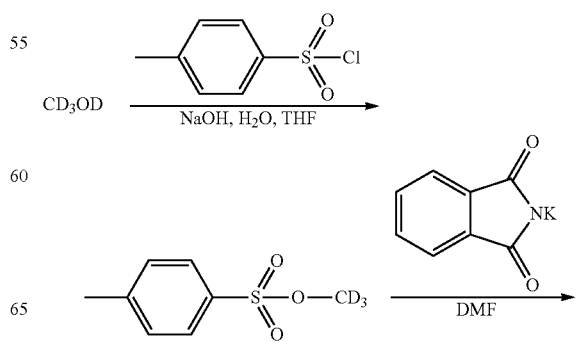

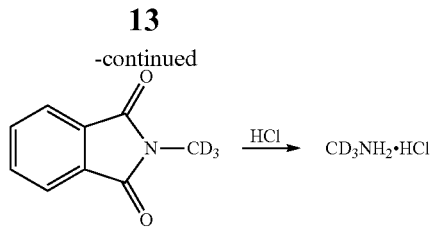

1. Preparation of (methyl-d₃) p-toluenesulfonate

To water (288 mL), sodium hydroxide (180 g, 4.5 mol, 5.0 eq) was added. At 0° C., methanol-d₃ (32.4 g, 900 mmol, 1.0 eq) was added, and the solution of tosyl chloride (206 g, 1.1 mmol, 1.2 eq) in tetrahydrofuran (288 mL) was dropwise added slowly. The mixture was warmed to room temperature and stirred overnight. The mixture was neutralized to neutral by dropwise adding acetic acid (206 g) at 25° C., filtered and partitioned. The aqueous phase was extracted with ethyl acetate (100 mL). The filter cake was dissolved in water (300 mL) and extracted with ethyl acetate (200 mL). The organic phases were combined and washed with saturated sodium carbonate (100 mL) and saturated brine (100 mL), dried over anhydrous sodium sulfate and filtered. The solvent in the filtrate was removed under reduced pressure to afford the title compound (160.5 g, purity 99%, yield 94%) as a pale yellow liquid.

$^1$H NMR(CDCl$_3$, 400 MHz): δ3.20 (s, 3H), 7.71-7.75 (m, 2H), 7.84-7.88 (m, 2H).

2. Preparation of N-(methyl-d₃)phthalimide

To N,N-dimethylformamide (DMF, 225 mL), potassium phthalimide (166.7 g, 0.9 mol, 2.0 eq) was added, and then methyl-d₃ p-toluenesulfonate (85.2 g, 0.45 mmol, 1.0 eq) was added dropwise at room temperature. The mixture was stirred at 60° C. for 0.5 hour, and filtered immediately. The solid was washed with DMF (250 mL and 100 mL) for two times. The DMF solutions were combined and water (1150 mL) was added dropwise at 0° C. to precipitate a white solid. The solid was filtered and washed with water (100 mL×2). The obtained solid was dried in vacuum to give the title compound (64 g, purity 99.6%, yield 85%) as a white solid.

$^1$H NMR (CDCl$_3$, 400 MHz): δ7.71-7.77 (m, 2H), 7.84-7.88 (m, 2H).

3. Preparation of (methyl-d₃)amine hydrochloride

To a solution of distilled water (625 mL) and concentrated hydrochloric acid (625 mL, 7.5 mol, 15 eq), N-(methyl-d₃) phthalimide (82 g, 0.5 mol, 1 eq) was added at room temperature, and the mixture was heated to 105° C. and refluxed overnight. The mixture was cooled to room temperature, filtered, and washed with distilled water (50 mL×2). Hydrochloric acid was removed under reduced pressure to afford a light yellow solid. To the solid was added anhydrous ethanol (140 mL). The mixture was refluxed for 1 hour, cooled to room temperature, and filtered. The solid was washed with ethanol (30 mL) and dried in vacuum to give the title compound (28 g, yield 80%) as a white solid.

$^1$H NMR (DMSO-d$_6$, 400 MHz): δ8.05 (br, 2H).

Example 5

Pharmacokinetic Evaluation in Rats 8 male Sprague-Dawley rats, (7-8 weeks old and body weight about 210 g), were divided into two groups, 4 in each group (rat No.: control group was 13-16; experimental group was 9-12), and orally administrated at a single dose at 3 mg/kg of either compound: (a) the undeuterated compound N-(4-chloro-3-(trifluoromethyl)phenyl)-N'-(4-(2-(N-methyl-aminoformyl)-4-pyridyloxy)phenyl)urea (control compound CM4306) or (b) N-(4-chloro-3-(trifluoromethyl)phenyl)-N'-(4-(2-(N-(methyl-d$_3$)-aminoformyl)-4-pyridyloxy)phenyl) urea (Compound CM4307 of the invention) prepared in Example 1. The pharmacokinetics differences of CM4306 and CM4307 were compared.

The rats were fed with the standard feed, given water and chlordiazepoxide. Chlordiazepoxide was stopped at the last night before experiment, and given again two hours after the administration of the compound. The rats were fasted for 16 hours before the test. The compound was dissolved in 30% PEG400. The time for collecting orbital blood was 0.083, 0.25, 0.5, 1, 2, 4, 6, 8 and 24 hours after administrating the compounds.

The rats were anaesthetized briefly by inhaling ether. A 300 μL orbital blood sample was collected into the tubes containing a 30 μL 1% heparin saline solution. The tubes were dried overnight at 60° C. before being used. After the blood samples were sequentially collected, the rats were anaesthetized by ether and sacrificed.

After the blood samples were collected, the tubes were gently reversed at least five times immediately to mix the contents sufficiently, and placed on the ice. The blood samples were centrifuged at 4° C. at 5000 rpm for 5 minutes to separate the serum and red blood cells. 100 μL, serum was removed to a clean plastic centrifugal tube by pipettor, and the name of the compound and time point were labeled on the tube. Serum was stored at −80° C. before LC-MS analysis.

The results showed that, compared with CM4306, the half-life (T$_{1/2}$) of CM4307 was longer [11.3±2.1 hours for CM4307 and 8.6±1.4 hours for CM4306, respectively], area under the curve (AUC$_{0-\infty}$) of CM4307 was significantly increased [11255±2472 ng·h/mL for CM4307 and 7328±336 ng·h/mL for CM4306, respectively], and apparent clearance of CM4307 was reduced [275±52 mL/h/kg for CM4307 and 410±18.7 mL/h/kg for CM4306, respectively].

The above results showed that, the compound of the present invention had better pharmacokinetics properties in the animal, and thus had better pharmacodynamics and therapeutic effects.

Example 6

The Pharmacodynamic Evaluation of CM4307 for Inhibiting Tumor Growth of Human Hepatocellular Carcinoma SMMC-7721 in Nude Mice Xenograft Model 70 Balb/c nu/nu nude mice, 6 weeks old, female, were bought from Shanghai Experimental Animal Resource Center (Shanghai B&K Universal Group Limited).

SMMC-7721 cells were commercially available from Shanghai Institutes for Biological Science, CAS (Shanghai, China).

The establishment of tumor nude mice xenograft model: SMMC-7721 cells in logarithmic growth period were cultured. After cell number was counted, the cells were suspended in 1×PBS, and the concentration of the cell suspension was adjusted to 1.5×10⁷/ml. The tumor cells were inoculated under the skin of right armpit of nude mice with a 1 ml syringe, 3×10⁶/0.2 ml/mice. 70 nude mice were inoculated in total.

When the tumor size reached 30-130 mm³, 58 mice were divided randomly into the different groups. The difference of the mean value of tumor volume in each group was less than 10% and drugs were started to be administrated.

The test doses for each group were listed in the following table.

| Group | Animal | Compounds | Administration | Dose (mg/kg) | Method |
|---|---|---|---|---|---|
| 1 | 10 | control (solvent) | Po | 0.1 ml/ 10 g BW | qd × 2 weeks |
| 2 | 8 | CM4306 | Po | 10 mg/kg | qd × 2 weeks |
| 3 | 8 | CM4306 | Po | 30 mg/kg | qd × 2 weeks |
| 4 | 8 | CM4306 | Po | 100 mg/kg | qd × 2 weeks |
| 5 | 8 | CM4307 | Po | 10 mg/kg | qd × 2 weeks |
| 6 | 8 | CM4307 | Po | 30 mg/kg | qd × 2 weeks |
| 7 | 8 | CM4307 | Po | 100 mg/kg | qd × 2 weeks |

Animal body weight and tumor size were tested twice a week during the experiment. Clinical symptoms were recorded every day. At the end of the administration, the tumor size was recorded by taking pictures. One mouse was sacrificed in each group and tumor tissue was taken and fixed in 4% paraformaldehyde. Observation was continued after the administration, and when the mean size of tumor was larger than 2000 mm³, or the dying status appeared, the animals were sacrificed, gross anatomy was conducted, and the tumor tissue was taken and fixed in 4% paraformaldehyde.

The formula for calculating the tumor volume (TV) is: $TV = a \times b^2/2$, wherein a, b independently represent the length and the breadth of the tumor. The formula for calculating the relative tumor volume (RTV) is: $RTV = V_t/V_0$, wherein $V_0$ is the tumor volume at the beginning of the administration, and $V_t$ is the tumor weight when measured. The index for evaluating the antitumor activity is relative tumor increment rate T/C (%), and the formula is: $T/C\,(\%) = (T_{RTV}/C_{RTV}) \times 100\%$, wherein $T_{RTV}$ is the RTV of the treatment group, and $C_{RTV}$ is the RTV of the negative control group.

Evaluation standard for efficacy: it is effective if the relative tumor increment rate T/C (%) is ≤40% and $p<0.05$ by statistics analysis.

The results showed that CM4306 and CM4307 were intragastric administrated every day for 2 weeks at doses of 10, 30, 100 mg/kg respectively, and both compounds showed the dose-dependent effect of the inhibition of tumor growth. At the end of administration, T/C % of CM4306 was 56.9%, 40.6% and 32.2%, respectively. T/C % of CM4307 was 53.6%, 40.8% and 19.6%. T/C % for 100 mg/kg dose groups was <40%, and tumor volume was significantly different ($p<0.01$) from the control group, indicating the significant effect in inhibiting tumor growth.

Compared with CM4306, the inhibitory efficacy of tumor growth at dosing 100 mg/kg of CM4307 was stronger (the T/C % for CM4307 and CM4306 is 19.6% and 32.2%, respectively, at day 15), there was significant difference in tumor volume between groups ($p<0.01$). Compared with CM4306, the absolute value of tumor inhibition rate for CM4307 increased more than 10%, the relative value increased about 60% (32.2%/19.6%−1=64%), and CM4307 showed more significant effect for inhibiting tumor growth.

In addition, during the experiment, no other drug-relevant toxic effects were observed.

All literatures mentioned in the present application are incorporated by reference herein, as though individually incorporated by reference. Additionally, it should be understood that after reading the above teaching, many variations and modifications may be made by the skilled in the art, and these equivalents also fall within the scope as defined by the appended claims.

What is claimed is:

1. A method for preparing (methyl-d₃)amine or salts thereof, wherein, comprises:
   (a2) in an inert solvent, reacting an alkali metal salt of phthalimide with compound A,

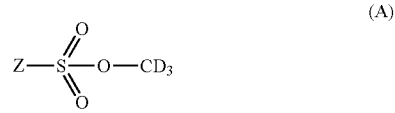

(A)

wherein, Z is CH₃, O-CD₃ or

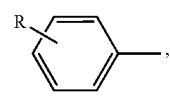

wherein R is methyl, nitro or halogen to form N-(methyl-d₃) phthalimide;

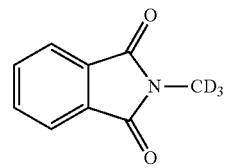 [SMILES: [2H]C([2H])([2H])N1C(=O)c2ccccc2C1=O]

step (b) reacting N-(methyl-d₃)phthalimide with an acid to form the salt of (methyl-d₃)amine; and
optional step (c): reacting the salt of (methyl-d₃)amine with a base to form (methyl-d₃)amine.

2. The method according to claim 1, wherein, in step (a2), said alkali metal salt of phthalimide is selected from the group consisting of potassium phthalimide, sodium phthalimide, lithium phthalimide, and a combination thereof.

3. The method according to claim 1, wherein, said acid is selected from the group consisting of hydrochloric acid, sulfuric acid, hydrobromic acid, trifluoroacetic acid, and a combination thereof.

4. A method for preparing (methyl-d₃)amine or salts thereof, wherein, comprises:
   (a1) in an inert solvent and in the presence of a catalyst, reacting phthalimide with deuterated methanol to form N-(methyl-d₃)phthalimide;

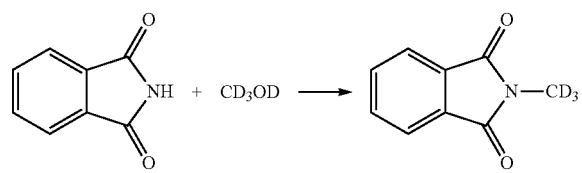

step (b) reacting N-(methyl-d₃)phthalimide with an acid to form the salt of (methyl-d₃)amine; and
optional step (c): reacting the salt of (methyl-d₃)amine with a base to form (methyl-d₃)amine.

5. The method according to claim 4, wherein, in step (a1), said acid is selected from the group consisting of hydrochloric acid, sulfuric acid, hydrobromic acid, trifluoroacetic acid, and a combination thereof.

6. The method according to claim 4, wherein, in step (a1), said inert solvent is tetrahydrofuran.

7. The method according to claim 4, wherein, in step (a1), said catalyst is selected from diethyl azodicarboxylate (DEAD), diisopropyl azodicarboxylate (DIAD), triphenylphosphine, tributylphosphine, or combination thereof.

* * * * *